United States Patent [19]

Ohbayashi

[11] Patent Number: 5,048,942
[45] Date of Patent: Sep. 17, 1991

[54] OPTICAL ELEMENT WITH REDUCED REFLECTANCE

[75] Inventor: Yasushi Ohbayashi, Shizuoka, Japan

[73] Assignee: Hamamatsu Photonics Kabushiki Kaisha, Shizuoka, Japan

[21] Appl. No.: 258,430

[22] Filed: Oct. 17, 1988

[30] Foreign Application Priority Data

Oct. 26, 1987 [JP] Japan .................. 62-269578

[51] Int. Cl.$^5$ .............................. G02B 1/10
[52] U.S. Cl. .................... 359/513; 359/507; 359/580; 359/894
[58] Field of Search ...................... 350/3.61, 164, 582, 350/588, 589, 319; 351/166

[56] References Cited

U.S. PATENT DOCUMENTS

| 2,220,862 | 11/1940 | Blodgett | 350/164 |
|---|---|---|---|
| 2,782,672 | 2/1957 | Osterberg | 350/164 |
| 3,438,539 | 4/1969 | Le Roy | 350/319 |
| 3,624,238 | 11/1971 | McKenzie | 351/166 |
| 3,836,193 | 9/1974 | Donahoe | 350/319 |
| 3,883,214 | 3/1975 | Hoffman | 350/319 |
| 3,998,531 | 12/1976 | Marzouk | 351/166 |
| 4,150,341 | 4/1979 | Ferguson | |
| 4,367,911 | 1/1983 | Graube | 350/3.61 |
| 4,372,652 | 2/1983 | Pontefract | 350/319 |
| 4,789,211 | 12/1988 | Wreede | 350/3.61 |
| 4,794,033 | 12/1988 | Ooi | 350/164 |
| 4,802,737 | 2/1989 | Denton | 350/164 |

OTHER PUBLICATIONS

Christensen; Defense Publication #T861,037; Apr. 22, 1969.
IEEE Journal of Quantum Electronics, vol. QE-21, No. 10, Oct. 1985, "Practical Urea Optical Parametric Oscillator for Tunable Generation Throughout the Visible and Near-Infrared," M. J. Rosker, K. Cheng, and C. L. Tang, pp. 1600-1606.
IEEE Journal of Quantum Electronics, vol. QE-14, No. 5, May 1978, "A Convenient Cell for Angle Tuned Nonlinear Optical Crystals," S. Blit and F. K. Tittel, pp. 329-330.

Primary Examiner—Bruce Y. Arnold
Assistant Examiner—David R. Parsons
Attorney, Agent, or Firm—Finnegan, Henderson, Farabow, Garrett, and Dunner

[57] ABSTRACT

In order to reduce the light reflectance, an optical element comprises an optical element body formed of an optical crystal or a lens, and glass members with a prescribed refractive index, wherein the glass member is bonded to each of the light incident and emergent surfaces of the element body by an adhesive agent with a prescribed refractive index. The optical element body will not be affected adversely even if it is made of a crystal which is vulnerable to heat.

8 Claims, 2 Drawing Sheets

000
OPTICAL ELEMENT WITH REDUCED REFLECTANCE

BACKGROUND OF THE INVENTION

The present invention relates to an optical device in which a surface of an element main body, such as an optical crystal or a lens, is given an anti-reflection processing.

In general, in an optical crystal or a lens the light intensity is diminished in consequence of the light reflection at the boundary surface. For instance, when the element body is formed of glass, the reflection loss at incident and emergent surfaces is, in total, about 8% for visible light. On the other hand, when it is formed of an optical crystal such as $LiNbO_3$ which has a refractive index of 2.2 to 2.3, the reflection loss amounts to about 30%. In order to decrease the power loss due to the surface reflection, it is necessary to apply an anti-reflection treatment to the incident and emergent surfaces of the optical crystal or the lens. As such a treatment, it has been conventional to form a transparent thin film of oxide on the light incident and emergent surfaces by means of sputtering or electron beam deposition. For example, 1 to 3 layers of transparent thin film of oxide with thickness of about 100 nm are formed on the glass or the optical crystal such as $LiNbO_3$. With the formation of such an oxide thin film, the reflection loss can be reduced to within 1%.

Now, when the oxide thin film is formed by the sputtering or the electron beam deposition, the surface of the optical crystal or the lens on which is formed the thin film is subjected to high temperature. For example, after the sputtering of 10 odd minutes, the temperature of the thin-film forming surface reaches higher than 200° C. As a result, if the optical crystal or the lens is formed of a thermally vulnerable material, such as one having a phase transition point in the low temperature range, it is impossible to directly form the thin film on the surface of element body, so that the anti-reflection treatment can not be performed. Moreover, when the thin film has not been formed in the desired manner, it becomes necessary to remove the film by some suitable method to form a new film again. This results in a problem that more labor is required to provide the anti-reflection treatment with desired performance.

SUMMARY OF THE INVENTION

It is accordingly an object of the present invention to provide an optical element with a structure which permits to apply an anti-reflection processing, without adversely affecting an element body such as an optical crystal or a lens.

It is another object of the present invention to provide an optical element with a simple structure that permits light to be outputted with high reliability, and is also adapted for miniaturization of the element.

An optical element according to the present invention comprises an optical element body and a glass member with a prescribed refractive index which is provided on light incident and emergent surfaces of the element body, wherein the glass member is bonded to the element body by a transparent adhesive material with a prescribed refractive index.

According to the present invention, a reflection loss at the boundary surface can be reduced by selecting appropriate refractive indices of the glass member and the adhesive material. Since assembling of the optical element requires a mere bonding of the glass member to the element body, the element body will hardly be affected even in the case where the element body is formed of a crystal which is vulnerable to heat. And, the optical element itself can be made compact. Furthermore, even in the case where the element body is a deliquescent crystal, the occurrence of deliquescence can be prevented provided that the surfaces of the element body other than the light incident and emergent surfaces are covered.

Other and further objects, features and advantages of the invention will appear more fully from the following description taken in connection with the accompanying drawings.

DETAILED DESCRIPTION OF THE PREFERRED EMBODIMENTS

Various embodiments of the invention will be described hereinafter with reference to the drawings.

Figure 1:
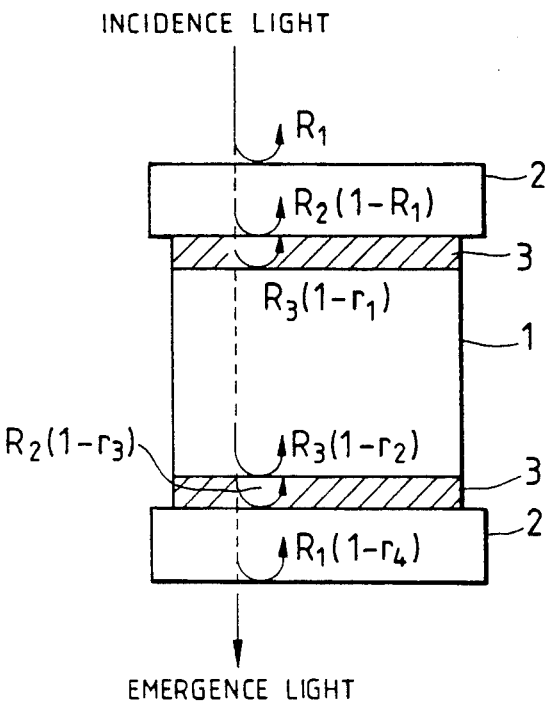
FIG. 1 is a diagram showing the first embodiment of an optical element in accordance with the present invention.

FIG. 1 is a compositional diagram for the first embodiment in accordance with the present invention.

An optical element shown in FIG. 1 includes an element body 1 and glass members provided on light incident and emergent surfaces of the element body, wherein the glass members 2 are bonded to the element body 1 by means of transparent adhesive 3. The element body 1 is formed, for example, of a nonlinear optical crystal which generates the second harmonic upon incidence of a laser beam on it. The glass member 2 is made, for example, of a glass plate, and the transparent adhesive 3 is made, for example, of generally used ultraviolet-curing-type agent.

If a $KNbO_3$ crystal is adopted as the element body 1 and the conventional anti-reflection treatment is applied with forming a thin film on it, there may be created cracks in the crystal because $KNbO_3$ has a phase transition point at 232° C. However, according to the present embodiment, the anti-reflection processing can be applied without heating the element body so that the element body will not be affected to any extent.

With the optical element of the above constitution, the description will be made about the reflection loss for the case where a $KNbO_3$ crystal is adopted as the element body 1. In the following description, the wavelength dispersion of refractive index will be ignored, and it will be assumed that the refractive index n of the crystal $KNbO_3$ is 2.3, the refractive index $n_1$ of the glass member 2 is 1.5, and the refractive index $n_2$ of the adhesive is 1.5.

First, the reflectance for the case where there alone exists the element body 1, that is, the $KNbO_3$ crystal, will be calculated. The reflectance R for one of the incident surface and the emergent surface is given by:

$$R = [(n_0 - n)/(n_0 + n)]^2$$
$$= [(1.0 - 2.3)/(1.0 + 2.3)]^2$$
$$= 0.155$$
(1)

where $n_0$ denotes a refractive index of the atmosphere. Neglecting the multiple reflections, the reflectance $R_{ef}$ which is caused by both of the incident surface and the emergent surface is given by:

$$R_{ef} = R + R(1-R) = 2R - R^2 = 0.286.$$
(2)

Therefore, the reflection loss amounts to about 29%.

In contrast to the above, in the case of bonding the glass members 2 to the element body by means of the adhesive 3, the reflectance $R_1$ for the boundary surface between the atmosphere and the glass member 2 is given by:

$$R_1 = [(n_0 - n_1)/(n_0 + n_1)]^2 = 0.04,$$
(3)

The reflectance $R_2$ for the boundary between the glass member 2 and the adhesive 3 is given by:

$$R_2 = [(n_1 - n_2)/(n_1 + n_2)]^2 = 0.$$
(4)

And the reflectance $R_3$ for the boundary between the adhesive 3 and the element body 1 is represented by:

$$R_3 = [(n_2 - n)/(n_2 + n)]^2 = 0.04.$$
(5)

Then, the resultant reflectance $R_{ef}$ for the total optical element, when the multiple reflections are disregarded, is given by:

$$R_{ef} = R_1 + R_2(1-R_1) + R_3(1-r_1) + R_3(1-r_2) + R_2(1-r_3) + R_1(1-r_4)$$
(6)

where $r_1$, $r_2$, $r_3$ and $r_4$ are given as follows:

$$r_1 = R_1 + R_2(1-R_1)$$
(7)

$$r_2 = r_1 + R_3(1-r_1)$$
(8)

$$r_3 = r_2 + R_3(1-r_2)$$
(9)

$$r_4 = r_3 + R_2(1-r_3).$$
(10)

Substituting the values determined by Eqs. (3), (4) and (5) in Eqs. (6) to (10), $$R_{ef} = 0.150$$
(11)

Therefore, the reflection loss becomes about 15%. Comparison of this result with the reflectance for the case of the element body 1 alone shows that the use of the glass members and the adhesive layers can reduce the reflection loss by about 14%.

Figure 2:
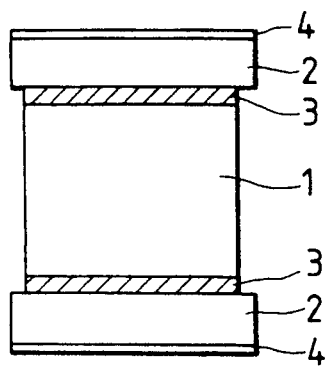
FIGS. 2 and 3 are diagrams showing respective modifications to the optical element given in FIG. 1.
Figure 3:
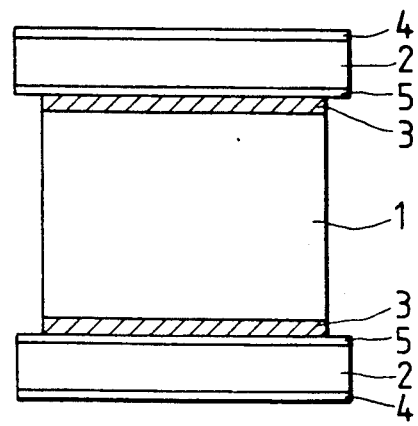

FIGS. 2 and 3 are diagrams showing respective modifications to the optical element given in FIG. 1. In the optical element shown in FIG. 1, there is not formed an anti-reflection coating on each of the glass members 2. In contrast, in the optical element shown in FIG. 2, there formed is a coating film 4 on the boundary surface between each of the glass members 2 and the atmosphere.

In the optical element shown in FIG. 3, there formed are a coating film 4 on the boundary between each of the glass members 2 and the atmosphere, and a coating film 5 on the boundary between each of the glass members 2 and the adhesive layer 3. In this modification, the adhesive 3 is changed to the one whose refractive index is almost equal to that of the $KNbO_3$ crystal (2.3) to make the reflectance $R_3$ substantially zero. Moreover, the coating film 5 has a characteristic which is appropriate to match both the glass member 2 ($n_1 = 1.5$) and the adhesive 3 ($n_2 = 2.3$) to keep the reflectance $R_2$ substantially zero.

As the material for the coating films 4 and 5, one may employ $MgF_2$ (n=1.38), $SiO_2$ (n=1.46) or $Al_2O_3$ (n=1.6) as a material with low refractive index, and $ZrO_2$ (n=2.0) or $TiO_2$ (n=2.2) as a material with high refractive index.

In the optical element of FIG. 2, by virtue of the coating film 4 the reflectance $R_1$ can be substantially reduced to zero so that the overall reflectance as determined by Eqs. (4) to (10) becomes:

$$R_{ef} = 0.078.$$
(12)

Therefore, the resultant reflectance is about 8% and the reflection loss can be decreased by about 21% compared with the case of the element body 1 alone.

Further, in the optical element in FIG. 3, the reflectances $R_1$, $R_2$ and $R_3$ can be substantially made to be zero by means of the coating films 4 and 5 and the adhesive 3, so that the overall reflectance $R_{ef}$ becomes:

$$R_{ef} \approx 0.$$
(13)

This indicates that it is possible to eliminate the reflection loss altogether.

Figure 4:
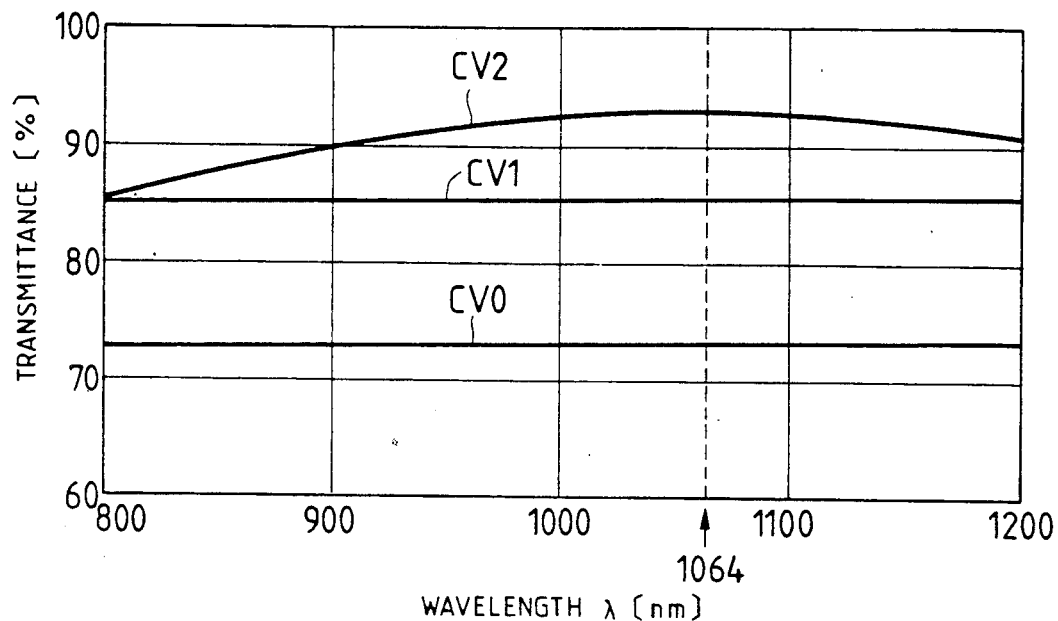
FIG. 4 is a graph showing theoretical transmittance curves.

FIG. 4 shows a comparison between the theoretical transmittance curves $CV_1$ and $CV_2$ obtained with the respective compositions shown in FIG. 1 and FIG. 2, and the theoretical transmittance curve $CV_0$ for the case of the crystal alone. It is assumed that the coating film 4 for the optical element shown in FIG. 2 is optimized for Nd:YAG laser (wavelength $\lambda = 1064$ nm). As is clear from FIG. 4, for the light with wavelength $\lambda$ of 1064 nm, for example, the transmittance is about 85% for the optical element of FIG. 1 and is about 9-3% for the optical element of FIG. 2, compared to about 73% for the case of the crystal alone, indicating the remarkable reduction of the reflection loss.

As described in the above, according to the first embodiment of the present invention, the reflection loss can be reduced by the mere bonding of glass members 2 with the prescribed refractive index to the element body 1 by using the adhesive 3 with the prescribed refractive index. Therefore, even if the element body 1 consists, for example, of a crystal which is vulnerable to heat, it becomes possible to readily apply the anti-reflection processing to the crystal without imparting heat to it.

Figure 5:
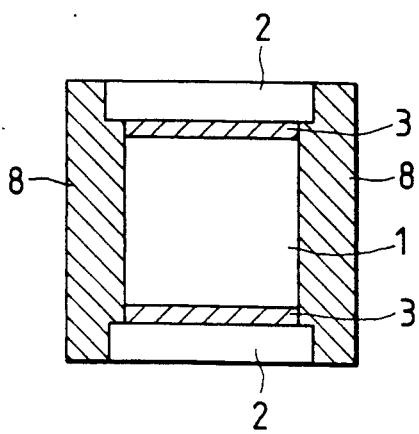
FIG. 5 is a diagram showing the second embodiment of an optical element in accordance with the present invention.

FIG. 5 is a compositional diagram for the second embodiment of the optical element in accordance with the present invention. In the optical element of FIG. 5, the glass members 2 are bonded to the light incident and emergent surfaces of the element body 1 by the transparent adhesive 3. In addition, remaining surfaces of the element body 1 are given a covering 8 of silicone rubber or the like so as to protect the entire surface of the element body from being exposed to the atmosphere. Again, the coating films 4 and 5 may be formed in advance, as needed, on one side or on both sides of each of the glass members 2.

With the above composition, the element body 1 can be protected, so that particularly in the case where the element body 1 is a deliquescent crystal such as a urea crystal or KDP, it is possible to effectively prevent the occurrence of deliquescence in the element body 1.

Figure 6:
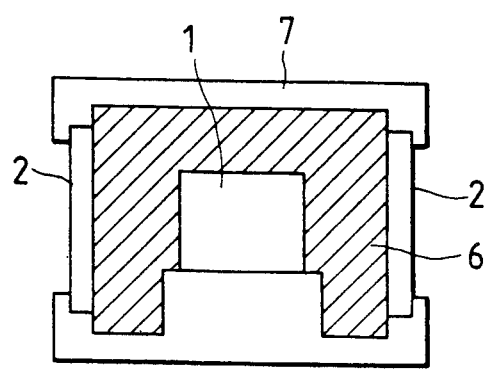
FIG. 6 is a compositional diagram for an optical element wherein a index-matching liquid is interposed between the element body and the glass members.

It should be noted that instead of bonding the element body 1 and the glass member 2 with the transparent adhesive 3, as in the optical elements in the first and the second embodiments in the foregoing, an optical element may be given a construction wherein an index-matching liquid 6 is interposed between the element body 1 and the glass members 2 and sealed in a cell 7, as illustrated in FIG. 6. In the optical element with such a construction, the matching liquid 6 plays a role similar to that of the adhesive 3 so that the reflection loss of the element body 1 can be reduced with a combination of the refractive indices of the glass member 2 and the matching liquid 6. This arrangement can be also applied to the crystal which is deliquescent or vulnerable to heat. However, the optical element of FIG. 6 requires the sealing of the matching liquid 6 within the cell 7, so that the entire structure of the element tends to be more complex and larger in size, giving rise to a disadvantage that its operation becomes cumbersome. Moreover, there is a problem that it is not possible to make the light emerge from the optical element 1 reliably with a pre-scribed accuracy because the glass members 2 are not closely adhered to the element body 1.

In contrast to this, the optical elements illustrated in FIGS. 1 to 3 and in FIG. 5 possess an extremely simple construction which permits to form the optical element small in size. And yet, the glass members 2 are bonded to the element body 1, so that they can make the light emerge with sufficiently high reliability.

As described in the foregoing, according to the preferred embodiments of the present invention, glass members are bonded to the light incident and emergent surfaces of the element body by the transparent adhesive. Therefore, it is possible to reduce the surface reflectance without adversely affecting the element body, and further, it is possible to make the construction of the opitcal element simpler which is adapted for rendering the element small in size, and to cause the light to emerge from the element with high reliability.

Various changes and modifications will become possible for those skilled in the art after receiving the teachings of the present disclosure without departing from the scope thereof.

What is claimed is:

1. An optical element comprising:
   an optical element body with a first refractive index, having a light incident surface and a light emergent surface, the optical element body being of a material that would be deleteriously changed by exposure to heat at a temperature generated by attempting to form a transparent oxide thin film on the material by sputtering or electron beam deposition;
   a first transparent optical member, having a second refractive index smaller than the first refractive index, and having a surface parallel to the light incident surface of the optical element body;
   a second transparent optical member, having the second refractive index, and having a surface parallel to the light emergent surface of the optical element body;
   a first transparent adhesive layer, having a third refractive index larger than the refractive index of air and no greater than the first refractive index, for bonding the first optical member to the optical element body; and
   a second transparent adhesive layer, having the third refractive index, for bonding the second optical member to the optical element body.

2. An optical element as claimed in claim 1, wherein said second and third refractive indices are substantially equal to each other.

3. An optical element as claimed in claim 1, wherein said first and third refractive indices are substantially equal to each other.

4. An optical element as claimed in claim 1, further comprising a first anti-reflection coating film on an outer boundary surface of said first transparent optical member and on an outer boundary surface of said second transparent optical member.

5. An optical element as claimed in claim 4, further comprising a second anti-reflection coating film on an inner boundary surface of said first optical member and on an inner boundary surface of said second optical member.

6. An optical element as in claim 1, wherein said first and second adhesive layers are of an ultraviolet curing type.

7. An optical element as claimed in claim 1, further comprising a covering for preventing surfaces of said optical element other than said light incident and emergent surfaces from being exposed to an atmosphere.

8. An optical element comprising:
   an optical element body including a deliquescent crystal with a first refractive index, having a light incident surface, a light emergent surface, and remaining surfaces;
   a first transparent optical member, having a second refractive index smaller than the first refractive index, and having a surface parallel to the light incident surface of the optical element body;
   a second transparent optical member, having the second refractive index, and having a surface parallel to the light emergent surface of the optical element body;
   a first transparent adhesive layer, having a third refractive index larger than the refractive index of air and no greater than the first refractive index, for bonding the first optical member to the optical element body;
   a second transparent adhesive layer, having the third refractive index, for bonding the second optical member to the optical element body; and
   covering means for preventing the remaining surfaces of the optical element body form being exposed to the atmosphere.

* * * * *